(12) United States Patent
Xu et al.

(10) Patent No.: US 9,468,623 B1
(45) Date of Patent: Oct. 18, 2016

(54) **MEDICAL USE OF COMPOUND FROM *GARCINIA ESCULENTA***

(71) Applicants: Hong Kong Baptist University, Hong Kong (HK); Shanghai University of Traditional Chinese Medicine, Shanghai (CN)

(72) Inventors: Hong-xi Xu, Shanghai (CN); Yuan-zhi Lao, Shanghai (CN); Zhi-jie Ding, Shanghai (CN); Hong Zhang, Shanghai (CN); Kai-xian Chen, Shanghai (CN); Hong-sheng Tan, Shanghai (CN); Zhao-xiang Bian, Hong Kong (HK); Cheng-yuan Lin, Hong Kong (HK); Shi-lin Chen, Beijing (CN); Da-jian Yang, Chongqing (CN); Ai-ping Lu, Hong Kong (HK); Albert Sun Chi Chan, Hong Kong (HK)

(73) Assignee: Hong Kong Baptist University, Hong Kong (HK)

(*) Notice: Subject to any disclaimer, the term of this patent is extended or adjusted under 35 U.S.C. 154(b) by 0 days.

(21) Appl. No.: 15/099,621

(22) Filed: Apr. 15, 2016

(30) Foreign Application Priority Data

Apr. 17, 2015 (CN) .......................... 2015 1 0184700

(51) Int. Cl.
*A61K 31/352* (2006.01)
(52) U.S. Cl.
CPC .................................. *A61K 31/352* (2013.01)
(58) Field of Classification Search
None
See application file for complete search history.

(56) References Cited

U.S. PATENT DOCUMENTS

2015/0038569 A1* 2/2015 Xu ....................... A61K 36/062
514/455

OTHER PUBLICATIONS

Shi et al., Molecules (2014), 19(2), pp. 1422-1431.*
Siegel R, Ma J, Zou Z, Jemal A (2014) Cancer statistics, 2014. CA Cancer J Clin 64: 9-29.
Simard EP, Ward EM, Siegel R, Jemal A (2012) Cancers with increasing incidence trends in the United States: 1999 through 2008. CA Cancer J Clin 62: 118-128.
Lin Y, Totsuka Y, He Y, Kikuchi S, Qiao Y, et al. (2013) Epidemiology of Esophageal Cancer in Japan and China. Journal of Epidemiology 23: 233-242.
Stoner GD, Gupta A (2001) Etiology and chemoprevention of esophageal squamous cell carcinoma. Carcinogenesis 22: 1737-1746.
Steeg PS (2006) Tumor metastasis: mechanistic insights and clinical challenges. Nature Medicine 12: 895-904.
Gaur P, Kim MP, Dunkin BJ (2014) Esophageal cancer: Recent advances in screening, targeted therapy, and management J Carcinog 13: 11.
Unnati S, Ripal S, Sanjeev A, Niyati A (2013) Novel anticancer agents from plant sources. Chinese Journal of Natural Medicines 11: 16-23.
Newman DJ, Cragg GM (2012) Natural Products as Sources of New Drugs over the 30 Years from 1981 to 2010. Journal of Natural Products 75: 311-335.
Li S, Jiang S, Jiang W, Zhou Y, Shen XY, et al. (2015) Anticancer effects of crocetin in human esophageal squamous cell carcinoma KYSE-150 cells. Oncol Lett 9: 1254-1260.
Wang JF, Feng JG, Han J, Zhang BB, Mao WM (2014) The molecular mechanisms of Tanshinone IIA on the apoptosis and arrest of human esophageal carcinoma cells. Biomed Res Int 2014: 582730.
Wang TT, Wang SK, Huang GL, Sun GJ (2012) Luteolin induced-growth inhibition and apoptosis of human esophageal squamous carcinoma cell line Eca109 cells in vitro. Asian Pac J Cancer Prev 13: 5455-5461.
Tian F, Fan T, Zhang Y, Jiang Y, Zhang X (2012) Curcumin potentiates the antitumor effects of 5-FU in treatment of esophageal squamous carcinoma cells through downregulating the activation of NF-kappaB signaling pathway in vitro and in vivo. Acta Biochim Biophys Sin (Shanghai) 44: 847-855.
Feng C, Zhou LY, Yu T, Xu G, Tian HL, et al. (2012) A new anticancer compound, oblongifolin C, inhibits tumor growth and promotes apoptosis in HeLa cells through Bax activation. Int J Cancer 131: 1445-1454.
Kan WL, Yin C, Xu HX, Xu G, To KK, et al. (2013) Antitumor effects of novel compound, guttiferone K, on colon cancer by p21Waf1/Cip1-mediated G(0) /G(1) cell cycle arrest and apoptosis. Int J Cancer 132: 707-716.
Lao Y, Wan G, Liu Z, Wang X, Ruan P, et al. (2014) The natural compound oblongifolin C inhibits autophagic flux and enhances antitumor efficacy of nutrient deprivation. Autophagy 10, p. 736-749.
Merza J, Aumond MC, Rondeau D, Dumontet V, Le Ray AM, et al. (2004) Prenylated xanthones and tocotrienols from Garcinia virgata. Phytochemistry 65: 2915-2920.
Chen RS, Song YM, Zhou ZY, Tong T, Li Y, et al. (2009) Disruption of xCT inhibits cancer cell metastasis via the caveolin-1/beta-catenin pathway. Oncogene 28: 599-609.
Napier KJ, Scheerer M, Misra S (2014) Esophageal cancer: A Review of epidemiology, pathogenesis, staging workup and treatment modalities. World J Gastrointest Oncol 6: 112-120.
Reagan-Shaw et al (2007) Dose translation from animal to human studies revisited. The FASEB Journal, 22, 659-661.

* cited by examiner

*Primary Examiner* — Brian J Davis
(74) *Attorney, Agent, or Firm* — Ella Cheong Hong Kong; Sam T. Yip

(57) ABSTRACT

The present invention provides compound extracted from *Garcinia* species and the use of said compound in preventing and treating cancer.

9 Claims, 12 Drawing Sheets

MEDICAL USE OF COMPOUND FROM *GARCINIA ESCULENTA*

FIELD OF INVENTION

The present invention relates to field of pharmaceuticals, particularly relates to medical use of a compound extracted from *Garcinia esculenta* and the pharmaceutical composition thereof.

BACKGROUND OF INVENTION

Esophageal cancer has a high mortality rate. China is one of the countries with the highest esophageal cancer incidence. There are two main forms of esophageal cancers, namely esophageal squamous cell carcinoma and adenocarcinoma. Squamous cell carcinoma accounts for 90% of the esophageal cancers. The main cause of death for esophageal cancer is metastasis; esophageal cancer metastasizes commonly to lungs, liver and bones. Despite the effort in developing treatments for esophageal cancer, due to the complexity of metastasis in esophageal cancer, existing treatments had not been promising. Thus, treatment of esophageal cancer remains a difficult issue.

Twenty-one *Garcinia* species are found in China, and located throughout southern provinces of Guangdong, Guangxi and Yunnan. Research shows *Garcinia* is an important source in search for anti-tumor drug candidates.

SUMMARY OF INVENTION

The present invention provides novel medical use of Griffipavixanthone extracted from *Garcinia esculenta*, pharmaceutical composition and health products comprising Griffipavixanthone.

The first aspect of the present invention provides a method of preventing and treating metastasis of esophageal cancer comprising providing a composition comprises a compound of Formula (I), or a pharmaceutically acceptable salt, prodrug or hydrate thereof.

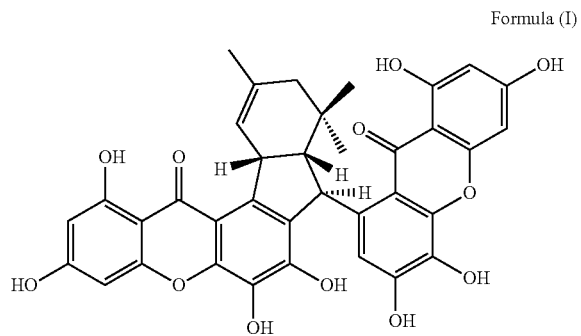

Formula (I)

In one embodiment, the composition consisting essentially of the compound of Formula (I), or the pharmaceutically acceptable salt, prodrug or hydrate thereof.

In another embodiment, said esophageal cancer is selected from human esophageal carcinoma cell Eca109 and human esophageal cancer cells KYSE150.

In yet another embodiment, said esophageal cancer metastasis is esophageal cancer metastasize to lungs.

In yet another embodiment, the composition comprises 1.62 mg compound of Formula (I), or a pharmaceutically acceptable salt, prodrug or hydrate thereof per kg of a subject in need thereof. The subject in need thereof includes human.

The second aspect of the present invention provides a method of preventing and treating esophageal cancer comprising providing a composition comprises a compound of Formula (I), or a pharmaceutically acceptable salt, prodrug or hydrate thereof.

In one embodiment, the composition consisting essentially of the compound of Formula (I), or the pharmaceutically acceptable salt, prodrug or hydrate thereof.

In another embodiment, said esophageal cancer is selected from human esophageal carcinoma cell Eca109 and human esophageal cancer cells KYSE150.

In yet another embodiment, the composition comprises 1.62 mg compound of Formula (I), or a pharmaceutically acceptable salt, prodrug or hydrate thereof per kg of a subject in need thereof. The subject in need thereof includes human.

The third aspect of the present invention provides a pharmaceutical composition for preventing esophageal cancer. The pharmaceutical composition comprises an effective amount of compound of Formula (I), or a pharmaceutically acceptable salt, prodrug or hydrate thereof.

The present invention also provides a health product for preventing esophageal cancer. The health product comprises an effective amount of compound of Formula (I), or pharmaceutically acceptable salt, prodrug or hydrate thereof.

In yet another embodiment, the health product comprises 1.62 mg compound of Formula (I), or a pharmaceutically acceptable salt, prodrug or hydrate thereof per kg of a subject in need thereof. The subject in need thereof includes human.

The present invention is described more fully in the following examples and embodiments and a variety of additional features, advantages and objectives of the invention would be clear to those skilled in the art.

DETAILED DESCRIPTION OF INVENTION

Figure 1:
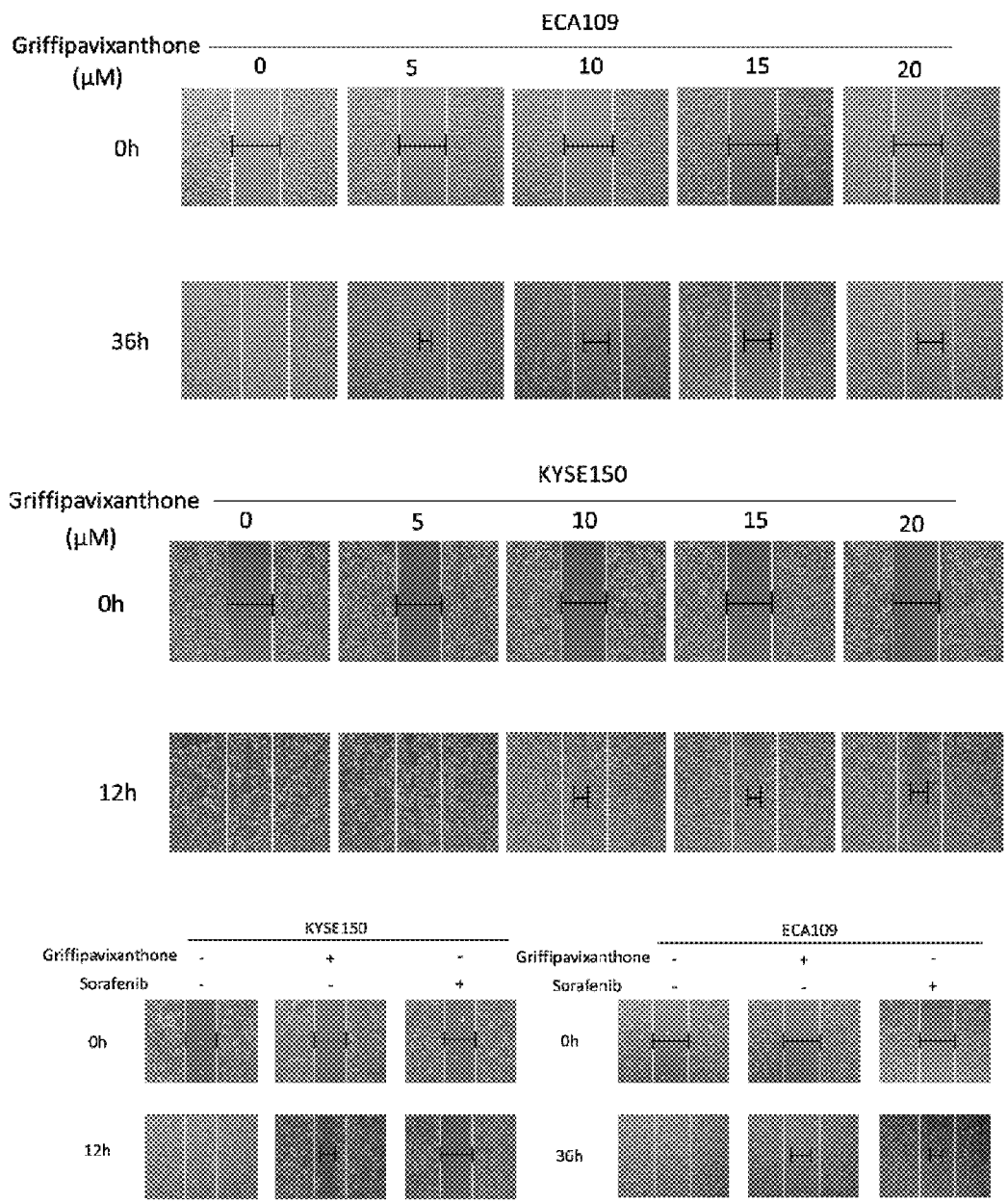
FIG. 1 shows micrograph of inhibition of Griffipavixanthone in Eca109 and KYSE150 cell lines, with Sorafeinib (SFB) as positive control, in a scratch migration essay.

The present invention is based on the discovery of the effect of compound Griffipavixanthone, extracted from *Garcinia* plant (*Garcinia esculenta*), to significantly inhibit growth, migration and invasion of esophageal cancer cells. The inventors of the present application discover that Griffipavixanthone is associated with anti-metastasis and anti-proliferation effects against esophageal cancer without promoting apoptosis in vitro. As a result, the present invention provides the use of Griffipavixanthone as a drug or health product for the prevention and treatment of esophageal cancer and metastasis thereof.

The first aspect of the present invention provides a method of preventing or treating esophageal cancer metastasis comprising a composition comprises a compound of Formula (I), or a pharmaceutically acceptable salt, prodrug or hydrate thereof.

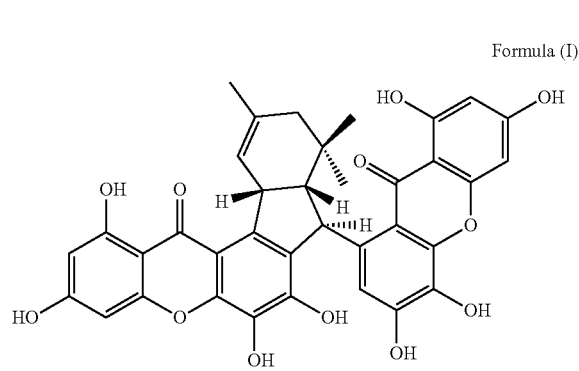

Formula (I)

In one embodiment, the composition consisting essentially of the compound of Formula (I), or the pharmaceutically acceptable salt, prodrug or hydrate thereof.

In another embodiment, said esophageal cancer is selected from human esophageal carcinoma cell Eca109 and human esophageal cancer cells KYSE150.

In yet another embodiment, said esophageal cancer metastasis is esophageal cancer metastasize to lungs.

In yet another embodiment, the composition comprises 1.62 mg compound of Formula (I), or a pharmaceutically acceptable salt, prodrug or hydrate thereof per kg of a subject in need thereof. The subject in need thereof includes human.

The second aspect of the present invention provides a method of preventing and treating esophageal cancer comprising providing a composition comprises a compound of Formula (I), or a pharmaceutically acceptable salt, prodrug or hydrate thereof.

In one embodiment, the composition consisting essentially of the compound of Formula (I), or the pharmaceutically acceptable salt, prodrug or hydrate thereof.

In another embodiment, said esophageal cancer is selected from human esophageal carcinoma cell Eca109 and human esophageal cancer cells KYSE150.

In yet another embodiment, the composition comprises 1.62 mg compound of Formula (I), or a pharmaceutically acceptable salt, prodrug or hydrate thereof per kg of a subject in need thereof. The subject in need thereof includes human.

The third aspect of the present invention provides a pharmaceutical composition for treating esophageal cancer. The pharmaceutical composition comprises an effective amount of compound of Formula (I), or pharmaceutically acceptable salt, prodrug or hydrate thereof.

The present invention also provides a health product for preventing esophageal cancer. The health product comprises an effective amount of compound of Formula (I), or a pharmaceutically acceptable salt, prodrug or hydrate thereof.

In yet another embodiment, the health product comprises 1.62 mg compound of Formula (I), or a pharmaceutically acceptable salt, prodrug or hydrate thereof per kg of a subject in need thereof. The subject in need thereof includes human.

The present invention provides a dimeric xanthone, Griffipavixanthone, having the following chemical structure:

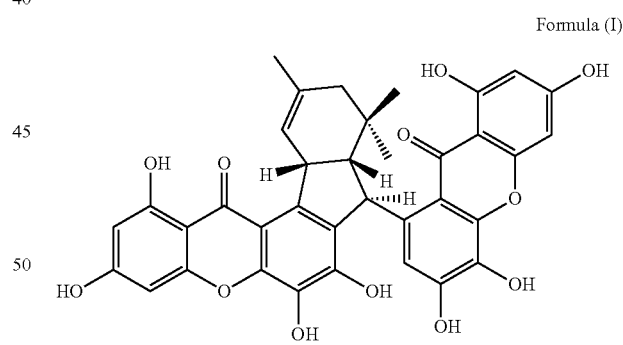

Formula (I)

Chemical Formula: $C_{36}H_{28}O_{12}$, Molecular weight: 652.62, CAS no.: 219649-95-3

Griffipavixanthone of the present invention is extracted from *Garcinia esculenta* Y. H. through conventional methods in the art. Griffipavixanthone is also commercially available, or is synthesized by conventional methods in the art. A skilled artisan in the art would know how to synthesize the compound of the present invention based on conventional knowledge in the art. The compound of the present invention may be further purified by column chromatography, high performance liquid chromatography or crystallization method. Purity of the compound is in accordance with pharmaceutical standards.

The compound of the present invention includes, but is not limited to optical isomers, racemates and other mixtures thereof. The optically active individual enantiomer or diastereomer may be obtained by asymmetric synthesis or by resolving racemates. Resolution of racemates by conventional methods may be used, such as crystallization in the presence of a resolving agent or using chiral high pressure liquid chromatography (HPLC). Further, compound of the present invention includes Z- and E-form (or cis- and trans-forms) of compounds having carbon-carbon double bond. Compound of the present invention has multiple tautomeric forms. The present invention includes all the tautomeric forms of the compound. The present invention also includes crystalline in the form of polymorphs and inclusions.

The compound of the present invention also includes crystalline and amorphous form thereof. The different forms of the compound comprises polymorphs, pseudo polymorphs, solvates, hydrates, unsolvated polymorphs (including anhydride)m conformational polymorphs, amorphous forms or a combination thereof. The terms "crystalline form", "polymorph" and "new form" may be used interchangeably in the present invention. The present invention intends to include all the crystalline and amorphous forms of the compound. Said crystalline and amorphous forms of the compound comprises polymorphs, pseudo polymorphs, solvates, hydrates, unsolvated polymorphs (including anhydride), conformational polymorphs, amorphous forms or a combination thereof, unless a particular crystalline or amorphous form is specified. The compound also includes pharmaceutically acceptable forms of the compounds; said pharmaceutically acceptable forms include chelates, non-covalent complexes, prodrugs or a mixture thereof.

"Pharmaceutically acceptable salts" include, but are not limited to inorganic acid salts such as hydrochloride, phosphate, diphosphate, hydrobromide, sulfate, sulfinate, nitrate and the like; organic acid salts such as malate, maleate, fumarate, tartrate, succinate, citrate, acetate, lactate, methanesulfonate, p-toluenesulfonate, 2-isethionate, benzoate, salicylate, stearate, and alkyl carboxylates such as acetates, wherein HOOC—$(CH_2)_n$—COOH, n=0-4 and the like. Similarly, pharmaceutically acceptable cations include, but are not limited to, sodium, potassium, calcium, aluminum, lithium and ammonium.

Further, if the above-described compound of the present invention is obtained as an acid addition salt; said salt is obtained through basifying an acid salt solution. Conversely, if the product is a free base, acid addition salts is prepared, according to conventional method, by dissolving a free base in a suitable organic solvent and treating said free base solution with an acid to produce addition salt, in particular pharmaceutically acceptable addition salts. Those skilled in the art will acknowledge a variety of synthetic methods for preparing a non-toxic pharmaceutically acceptable addition salts.

As described above, prodrugs also fall within the scope of the compound of the present invention. In some embodiments, the term "prodrug" includes any compounds that convert to the compound of formula (I) when the prodrug administered to a patient, or any compounds that is metabolized to the compound of Formula (I). Examples of prodrug include functional carboxylic acid derivatives of the compound of Formula (I). Examples of the carboxylic acid prodrug include, but are not limited to, carboxylic acid esters, such as alkyl esters, hydroxyalkyl esters, arylalkyl esters and aryloxyalkyl esters.

"Solvate" is formed by the interaction between a solvent and a compound. The term "compound" is intended to include solvates of the compound. Similarly, "salts" comprises salts of solvates. Suitable solvates are pharmaceutically acceptable solvates, such as hydrates and hemihydrates.

"Chelate" is formed by a compound with two or more coordinated metal ions. The term "compound" is intended to include chelate of the compound of Formula (I). Similarly, "salts" includes chelate form of the salt.

"Non-covalent complex" is formed by one compound interacting with another molecule, wherein said compound and molecule do not form a covalent bond. For example, interaction by van der Waals forces, hydrogen bonding and electrostatic interaction (also called ionic bonding). Such non-covalent complexes are also included in the term "compound" of the present invention.

Griffipavixanthone of the present invention may be used alone or used in the form of a pharmaceutical composition. Pharmaceutical composition comprises Griffipavixanthone as the active ingredient and a pharmaceutical carrier. Preferably, the pharmaceutical composition of the present invention comprises 0.1-99.9% by weight of Griffipavixanthone. "Pharmaceutical carrier" does not affect the pharmaceutical activity of Griffipavixanthone, and the amount of carrier is not toxic to humans.

The pharmaceutically acceptable carriers include, but are not limited to: lecithin, aluminum stearate, alumina, ion exchange material, self-emulsifying drug delivery system, Tween or other surface active agent, serum proteins, buffer substances such as phosphates, amino acid, sorbic acid, water, salts, electrolytes such as protamine sulfate, disodium hydrogen phosphate, potassium hydrogen phosphate, sodium chloride, zinc salts, magnesium silicate, partially saturated glyceride mixtures or the like.

The composition of the present invention also includes other commonly used pharmaceutical excipients, such as binder (e.g. microcrystalline cellulose), filler (e.g. starch, glucose, anhydrous lactose and lactose beads), disintegrating agent, (e.g. cross-linked PVP, cross-linked sodium carboxymethyl starch, cross-linked carboxymethyl sodium cellulose, low substituted hydroxypropylcellulose), lubricant (e.g. magnesium stearate) and absorption accelerators, adsorption carrier, flavouring agents, sweeteners, excipients, diluents, wetting agents and the like.

Griffipavixanthone and the pharmaceutical composition of the present invention may be prepared by conventional methods in the art and may be administered via enteral, parenteral or topical routes. Oral formulations include capsules, tablets, liquids, granules, pills, powders, pellets, pastes and the like; parenteral administration includes injections and the like; topical formulations include creams, patch, ointment, sprays and the like. Preferably, the present invention is administered orally.

Griffipavixanthone and the pharmaceutical composition of the present invention may be administered orally, sublingually, transdermally, intramuscularly or subcutaneously, mucocutaneously, as well as via vein, urethra, vagina and the like.

In addition to pharmaceutical formulation, antioxidants, pigments, enzymes and other food additives may be added to Griffipavixanthone of the present invention to prepare health product according to convention methods.

Hereinafter the present invention will be described in detail with reference to specific embodiments. However, one skilled in the art will appreciate, the particular embodiments only serve to explain the present invention more clearly, in any case should not be construed as a limitation of the present invention. Experimental methods of the below examples do not indicate any specific conditions; are based on conventional conditions or conditions in accordance with the manufacturer recommendations. Unless otherwise specified, all percentages, ratios, proportions, or parts are calculated by weight.

Unless otherwise specified, all scientific terminology is the same as those understood by those skilled in the art. In addition, any methods, materials similar or related to the present invention may also be applicable. The preferred embodiments described herein are for demonstration purposes only.

The above mentioned features of the invention, or the features mentioned in the below examples may be combined. All of the features disclosed in this patent specification can be used in any combination; features disclosed in the present specification may be substituted with any other alternatives which can provide the same characteristics or similar purpose. Therefore, unless otherwise stated, the disclosed features are mere general examples.

EXAMPLES

Example 1

Extraction of Griffipavixanthone from *Garcinia esculenta*

1.1 Materials

*Garcinia esculenta* twigs specimens are collected in Nuijiang, Yunnan Province, China in August 2010. Professor Zhou Yuanchuan (Yunnan University of Traditional Chinese Medicine) identified the specimen as a branch of *Garcinia esculenta* Y.H.L. The specimens (herbarium no.: 20100801) is deposited at the Innovative Research Laboratory of TCM, Shanghai University of Traditional Chinese Medicine.

1.2 Methods

Air-dried and powdered twigs of *Garcinia esculenta* (4 kg) are extracted with petroleum ether (5×20 L, duration of 2 days for each extraction). Extracts are combined and evaporated to dry under vacuum to produce a petroleum ether-soluble part (fraction I, 40 g). The remaining materials are refluxed with 80% EtOH (v/v, 5×20 L). Extracts of the remaining materials are combined and evaporated to dry under vacuum to give a residue, and the residue is suspended in $H_2O$ (5 L) and extracted with EtOAc (5×5 L) to obtain fractions II (50 g, the EtOAc-soluble part) and III (the remainin $H_2O$ portion), respectively. The remaining materials are refluxed with distilled water (5×20 L) to afford the $H_2O$-soluble part (fraction IV).

Fraction II is subjected to column chromatography on MCI, is eluted with 30%, 60%, 90%, 100% EtOH, and EtOAc, successively, to obtain subfractions IIA-IIE, respectively. Fraction IIC (14 g) is separated using a reversed-phase C18 silica gel column and is eluted with MeOH—$H_2O$ (60:40 to 100:0) as a gradient system to give nine subfractions (IIC1-IIC9). Fraction IIC6 is chromatographed over reversed-phase C18 silica gel and is eluted with MeOH—$H_2O$ in a gradient (45:55 to 100:0) to afford subfractions IIC6a-IIC6d. Fractions IIC6c is purified by Sephadex LH-20, and is eluted with MeOH to obtain Griffipavixanthone (108 mg).

1.3 Results

Griffipavixanthone extracted from *Garcinia esculenta* is confirmed with below chemical structure, Formula (I), using NMR and mass spectrometry.

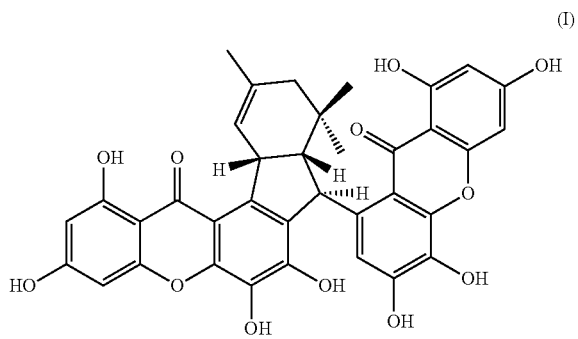

(I)

Example 2

Griffipavixanthone Inhibits Human Esophageal Cancer Cell Motility in Wound Healing 2.1 Materials Human esophageal cancer cell Eca109 purchases from Shanghai Institute of Biochemistry and Cell Biology (Shanghai, China); KYSE105 are given from Fudan University Shanghai Cancer Center.

RPMI1640 is purchased from Hyclone (Logan, Utah, USA), fetal calf serum, penicillin and streptomycin are purchased from Invitrogen Corporation, Sorafenib is purchased from Selleck Chemicals.

2.2 Methods

Eca109 and KYSE150 are cultured in RPMI1640 medium supplemented with 10% fetal calf serum, 100U/ml penicillin and 100 μg/ml streptomycin in a humidified atmosphere containing 5% $CO_2$ at 37° C. 0.25% trypsin is used for digestion and passage; cells under logarithmic growth phase are used in the experiment.

Eca109 and KYSE150 under logarithmic growth phase are seeded into 24-well plate ($1\times10^5$ cells/well). When monolayer of cell is formed, use a sterile 100 μl pipette tip to create a scratch on the monolayer, and fresh medium containing different concentration of Griffipavixanthone (GPX) or Sorafenib (SFB) (20 μM/well) are added. Cells are observed at 12 hours and 36 hours after scratch and imaged under IX83 microscope (Olympus, Tokyo, Japan).

2.3 Results

As seen in FIG. 1, GPX and SFB significantly inhibit cell scratch migration. GPX inhibits cell migration of Eca109 and KYSE150 in wound healing in a dose dependent manner. The same wound healing suppression is observed in cells treated with Sorafenib.

Example 3

GPX Inhibits Human Esophageal Cancer Cell Migration 3.1 Materials

RPMI1640 is purchased from Hyclone, fetal calf serum, penicillin and streptomycin are purchased from Invitrogen Corporation. Transwell chambers is purchased from Corning (NY, USA).

3.2 Methods

Eca109 and KYSE150 are cultured in RPMI1640 medium supplemented with 10% fetal calf serum, 100U/ml penicillin and 100 μg/ml streptomycin in a humidified atmosphere containing 5% $CO_2$ at 37° C. 0.25% trypsin is used for digestion and passage; cells under logarithmic growth phase are used in the experiment.

Figure 3:
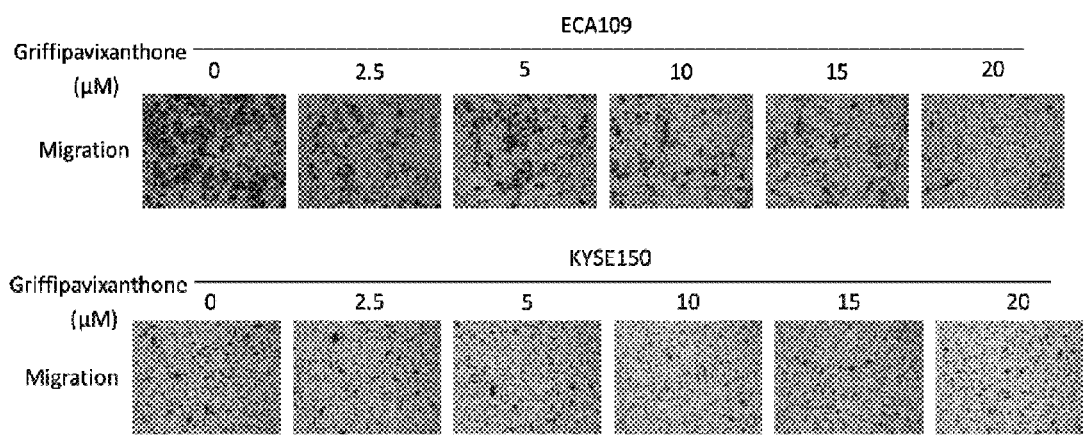
FIG. 3 shows staining of cell migration of Eca109 and KYSE150 after 24 hours of Griffipavixanthone treatment of various concentrations

Eca109 and KYSE150 ($5 \times 10^4$ cells/well) are seeded to the upper chamber (8 μm pore size) of the transwell chambers. The upper chamber contains serum-free; the lower chamber contains 10% FBS. Cells are treated with GPX for 24 hours, medium is then removed, non-migrated cells found on the upper chamber are removed using a cotton swab. Migrated cells found on the bottom chamber are fixed with 4% paraformaldehyde, stained with 0.1% crystal violet and scored under a light microscope in five random fields as shown in FIG. 3. Experimental data are expressed as mean±standard deviation, using SPSS18.0 statistical software for analysis, One-Way ANOVA for variance, comparison using Student t test, P<0.01, *P<0.001 is considered as statistically significant difference.

3.3 Results

Figure 2:
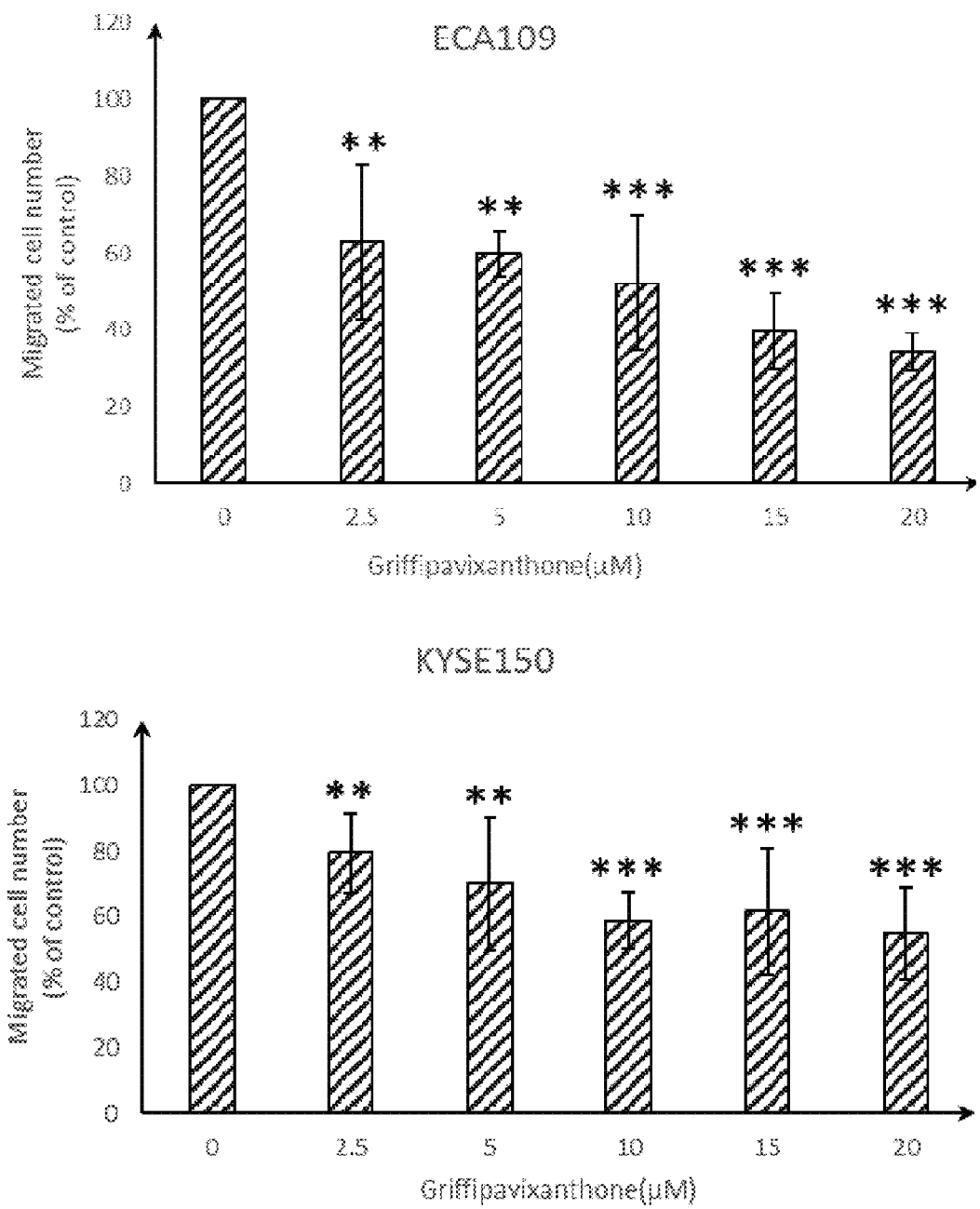
FIG. 2 is bar charts showing statistical analysis of cell migration of Eca109 and KYSE150 after 24 hours of Griffipavixanthone treatment of various concentrations (P<0.01, * P<0.001). Vertical axis represents the percentage of migrated cells (compared with the control group). Horizontal axis represents concentration of Griffipavixanthone

As seen in FIG. 2 and FIG. 3, GPX inhibits cell migration of Eca109 and KYSE150 at 5, 10, 15, 20 μM in a dose dependent manner.

Example 4

Griffipavixanthone Inhibits Human Esophageal Cancer Cell Invasion 4.1 Materials

RPMI1640 is purchased from Hyclone, fetal calf serum, penicillin and streptomycin are purchased from Invitrogen Corporation. Transwell chambers is purchased from Corning. Matrigel is purchased from BD Biosciences (Bedford, Mass., USA).

4.2 Methods

Eca109 and KYSE150 are cultured in RPMI1640 medium supplemented with 10% fetal calf serum, 100U/ml penicillin and 100 μg/ml streptomycin in a humidified atmosphere containing 5% $CO_2$ at 37° C. 0.25% trypsin is used for digestion and passage; cells under logarithmic growth phase are used in the experiment.

Transwell chambers (8 μm pore size) used in cell migration assay are pre-incubated with matrigel for 2 hours, Eca109 ($1 \times 10^5$ cells/well) are seeded onto serum-free upper chambers, lower chamber contains 10% FBS medium. Cells are treatment with GPX for 24 hours, thereafter, medium is discarded, cotton swab is used to gently remove the non invaded cells in the upper chamber. Invaded cells in the lower chamber are fixed with 4% paraformaldehyde, stained with 0.1% crystal violet and scored under a light microscope. Experimental data are expressed as mean±standard deviation, using SPSS18.0 statistical software for analysis, One-Way ANOVA for variance, comparison using Student t test, *P<0.05, P<0.01, *P<0.001 is considered as statistically significant difference.

4.3 Results

Figure 4:
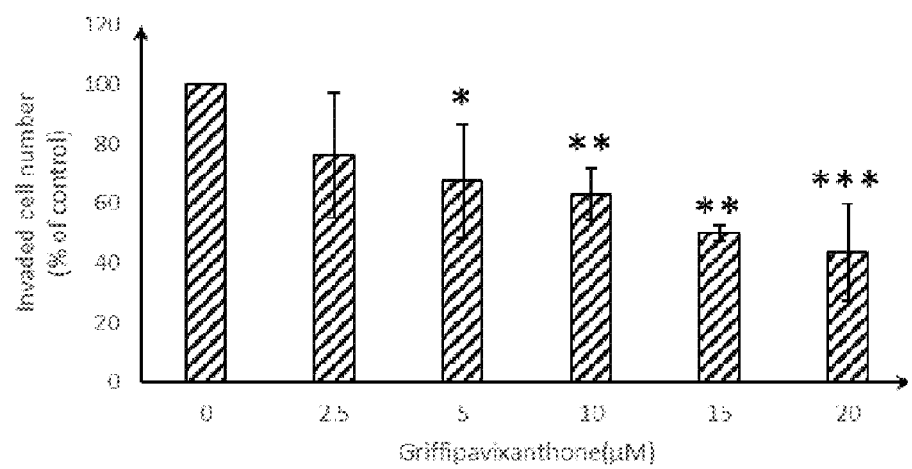
FIG. 4 is bar charts showing statistical analysis of cell invasion essay of Eca109 and KYSE150 after 24 hours of Griffipavixanthone treatment (*P<0.05, P<0.01, *P<0.001). Vertical axis represents the percentage of cells that has passed through the basement membrane (compared with control group). Horizontal axis represents concentration of Griffipavixanthone.
Figure 4:
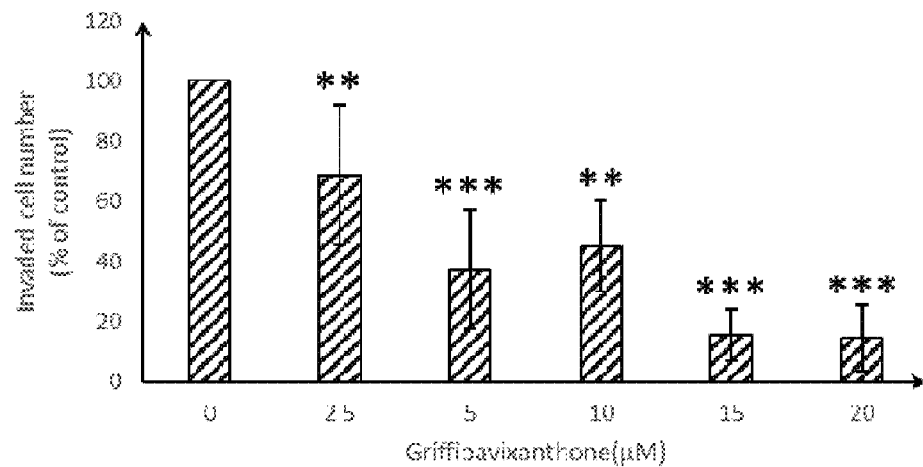
Figure 5:
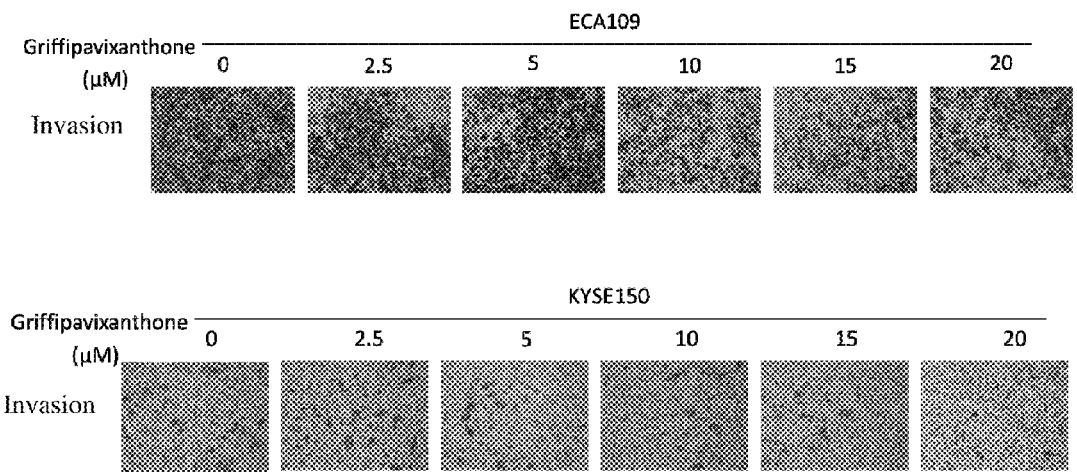
FIG. 5 shows staining of cell invasion essay of Eca109 and KYSE150 cells after 24 hours of Griffipavixanthone treatment of various concentrations.

As seen in FIG. 4 and FIG. 5, GPX inhibits cell invasion of Eca109 and KYSE150 at 5, 10, 15, 20 μM in a dose dependent manner. Experimental data are expressed as mean±standard deviation, using SPSS18.0 statistical software for analysis, One-Way ANOVA for variance, comparison using Student t test, *P<0.05, P<0.01, *P<0.001 is considered as statistically significant difference.

Example 5

Griffipavixanthone Inhibits Human Esophageal Cancer Cell Proliferation 5.1 Materials RPMI1640 is purchased from Hyclone, fetal calf serum, penicillin and streptomycin are purchased from Invitrogen Corporation.

5.2 Methods

Eca109 and KYSE150 are cultured in RPMI1640 medium supplemented with 10% fetal calf serum, 100U/ml penicillin and 100 μg/ml streptomycin in a humidified atmosphere containing 5% $CO_2$ at 37° C. 0.25% trypsin is used for digestion and passage; cells under logarithmic growth phase are used in the experiment.

Eca109 (500 cells/well) and KYSE150 (250 cells/well) are seeded in a 6-well plate. Cells are then treated with GPX or SFB (20 μM/well) for 48 hours, and continue to be incubated for 7 days. On the $7^{th}$ day, cells are fixed with 4% paraformaldehyde, stained with 0.1% crystal violet and imaged under a light microscope.

5.3 Results

Figure 6:
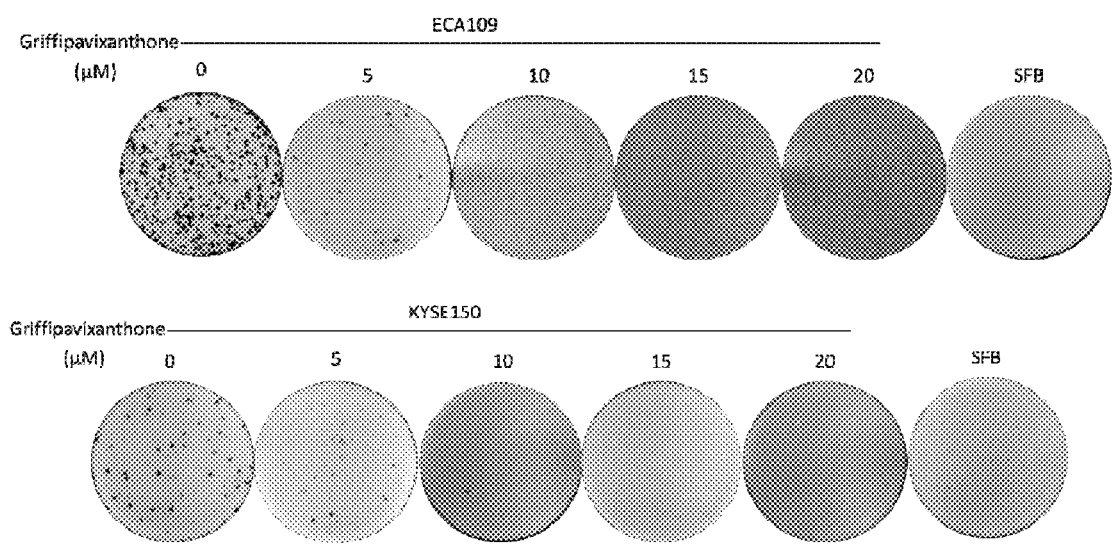
FIG. 6 shows staining of cell proliferation of Eca109 and KYSE150 after 48 hours of Griffipavixanthone treatment.
Figure 7A:
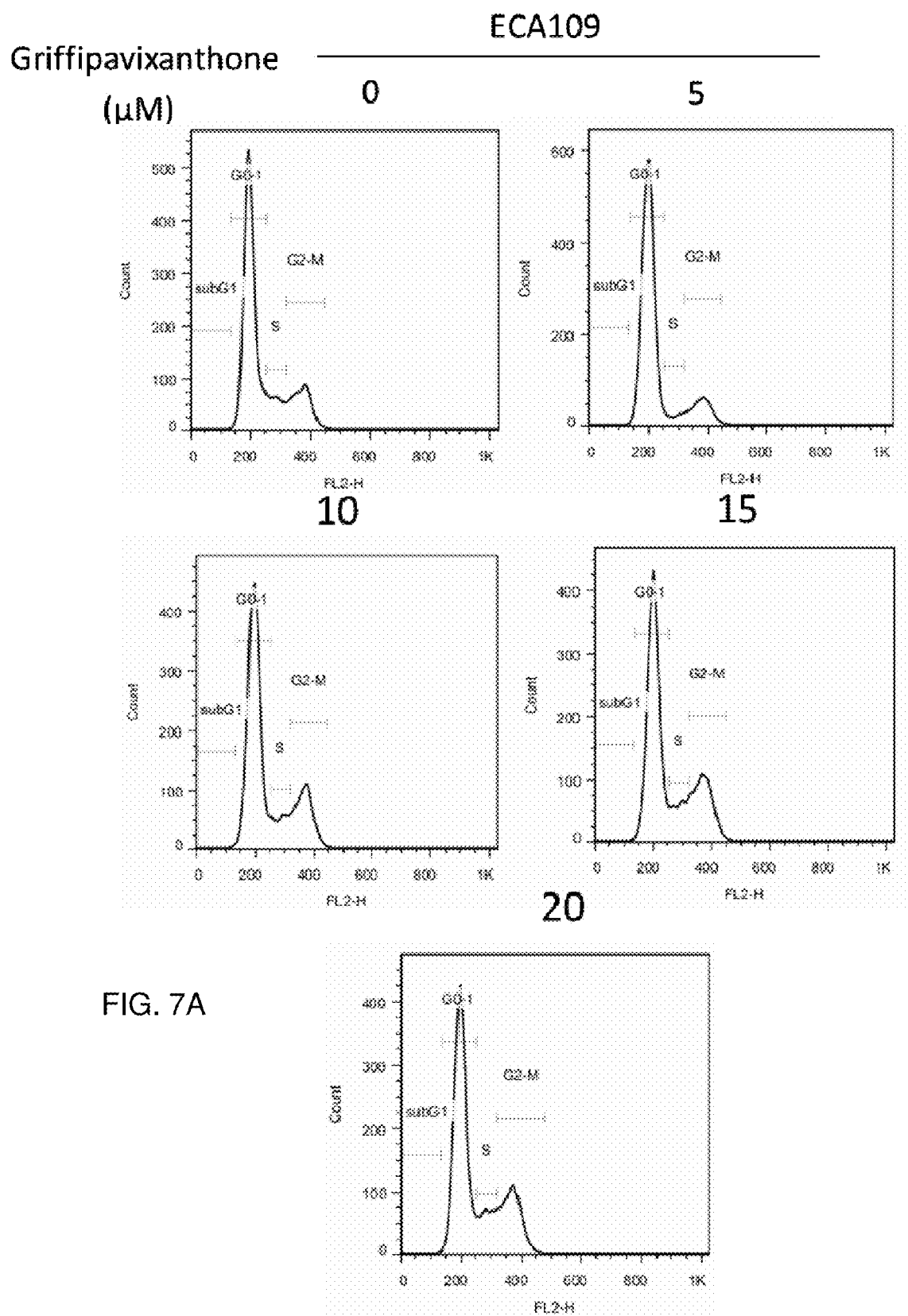
FIG. 7 shows flow cytometric analysis of G2/M cell cycle arrest of Eca109 and KYSE150 cells after 48 hours of Griffipavixanthone (FIG. 7A and FIG. 7B) and Sorafenib (positive control, FIG. 7C and FIG. 7D) treatment.
Figure 7B:
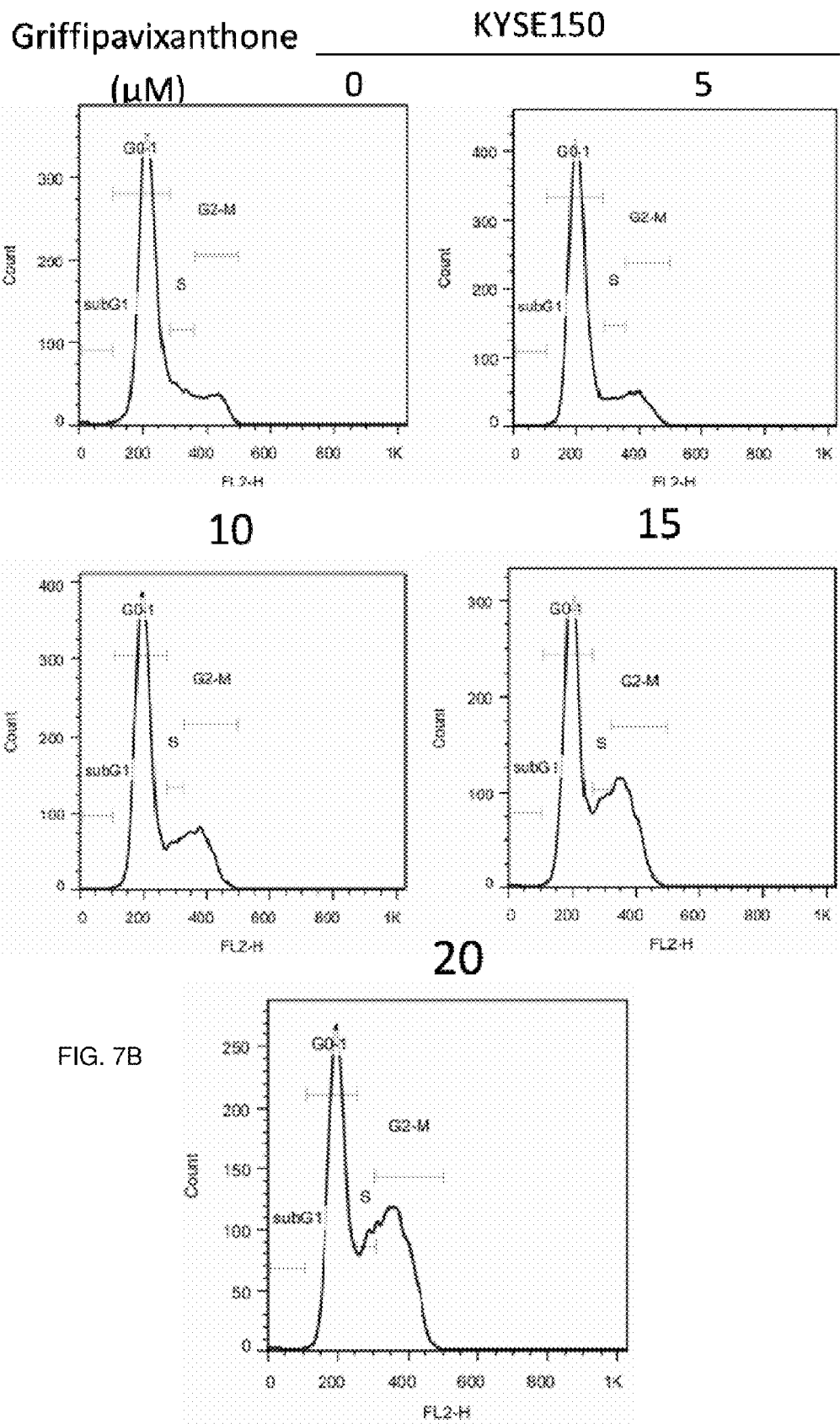
Figure 7C:
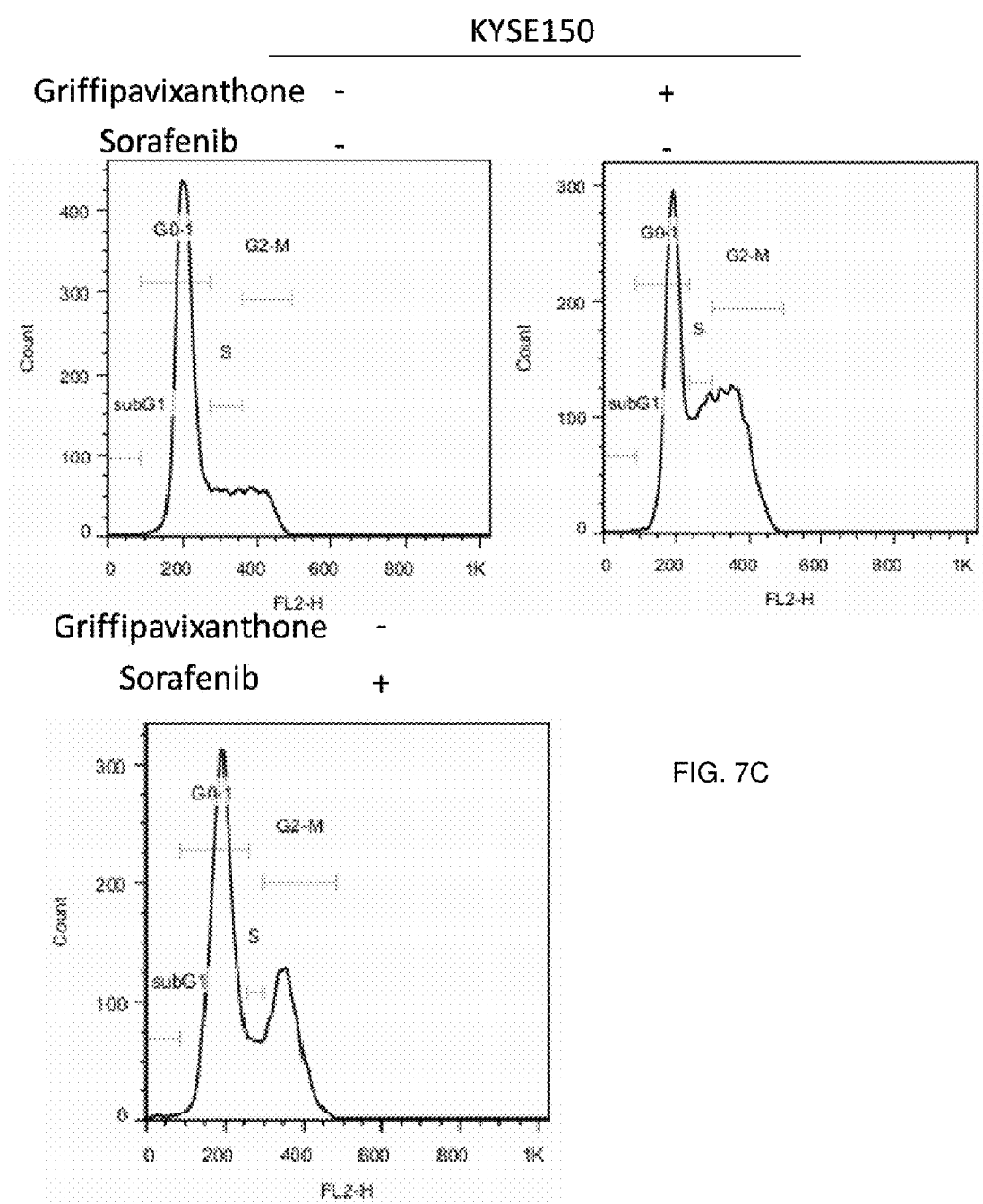
Figure 7D:
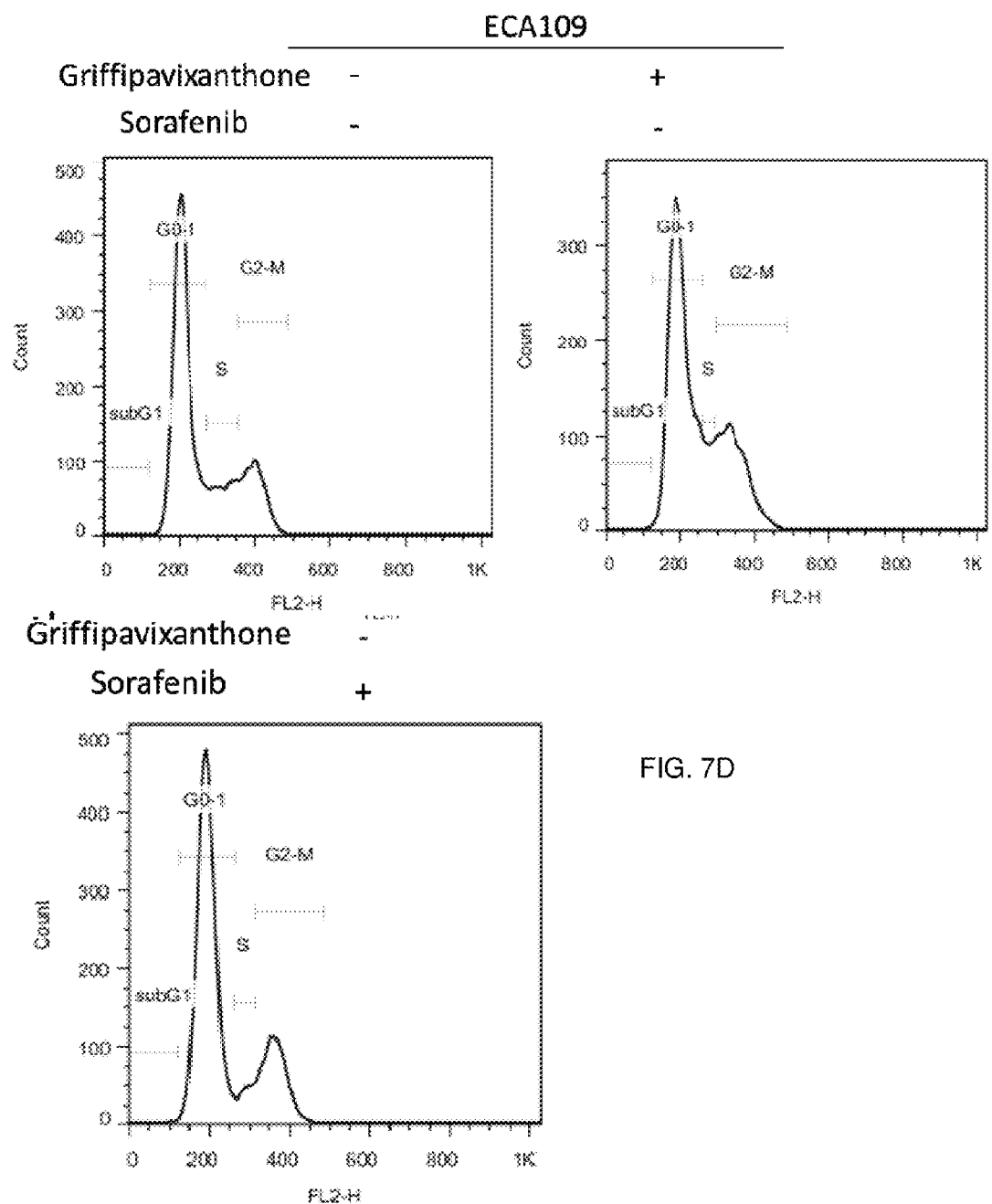
Figure 8A:
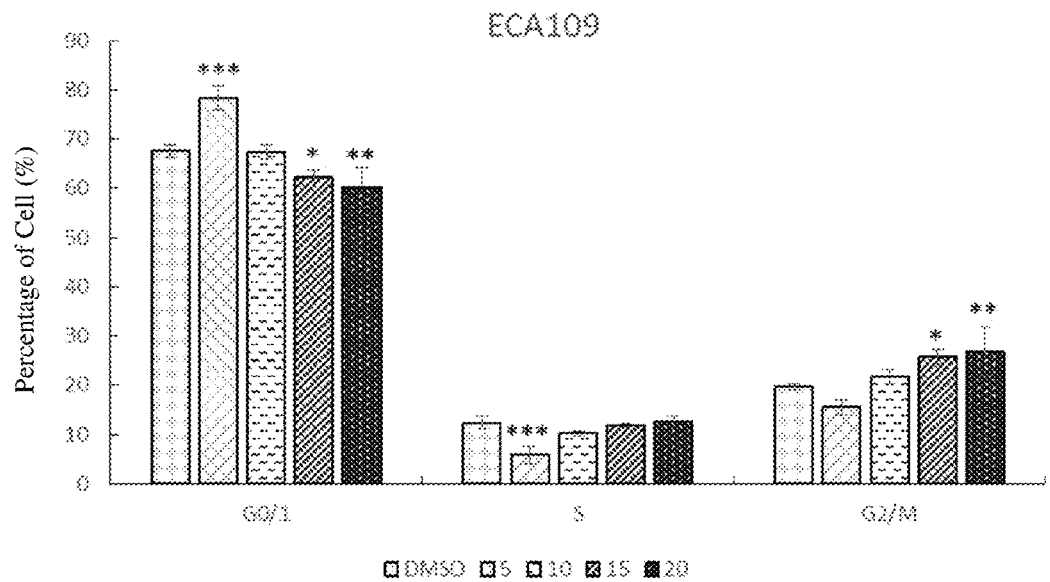
FIG. 8 are bar charts showing statistical analysis of cell cycle arrest of ECa109 and KYSE150 cells induced by Griffipavixanthone (FIG. 8A and FIG. 8B) and Sorefenib treatment (FIG. 8C and FIG. 8D).
Figure 8B:
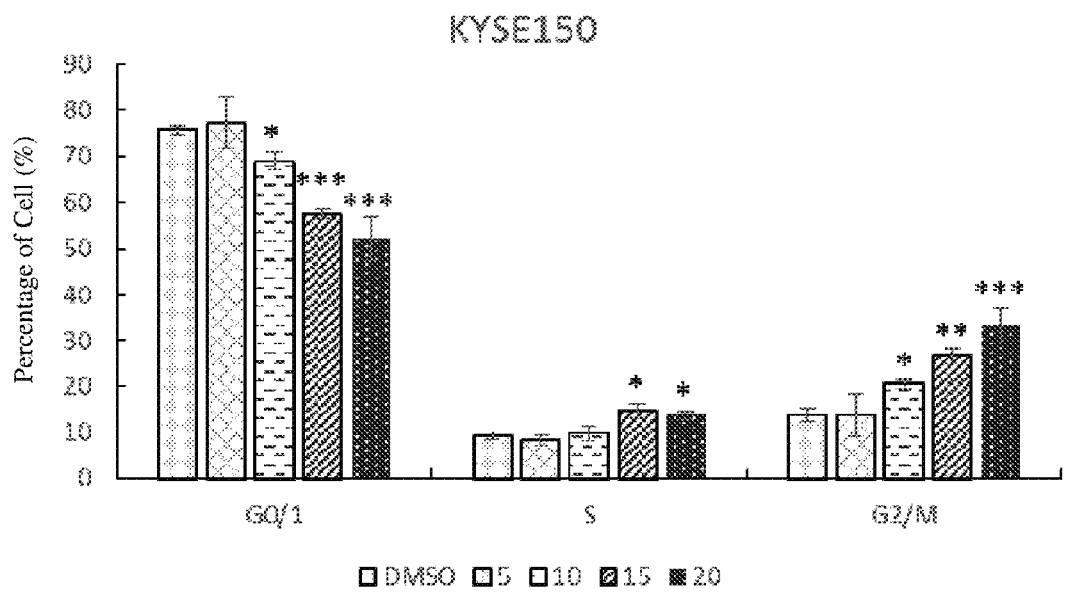
Figure 8C:
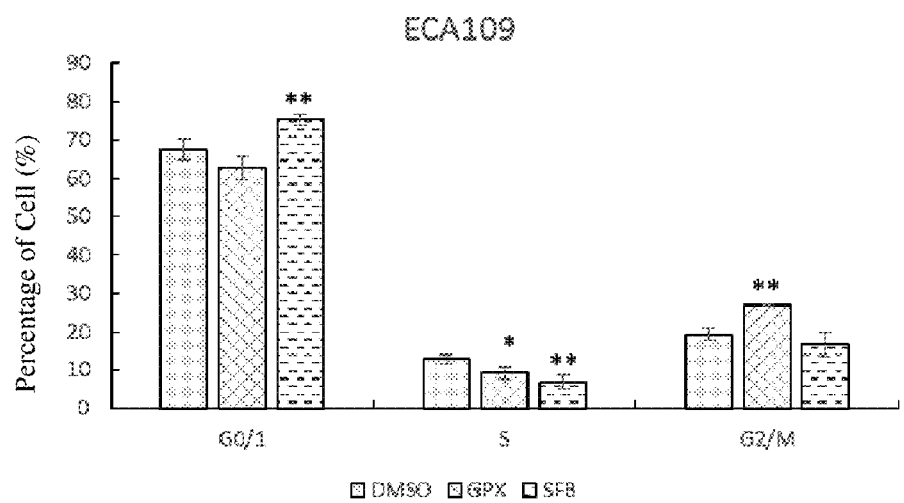
Figure 8D:
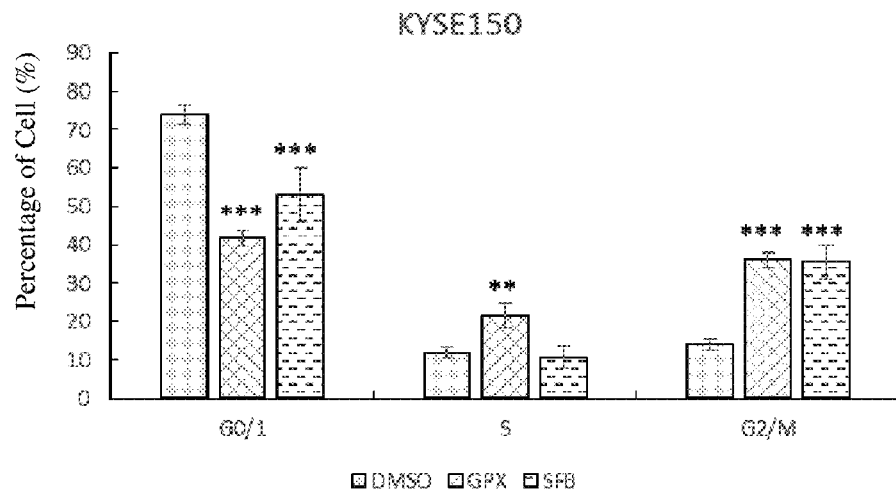

As shown in FIG. 6, esophageal cancer cell colony formation is inhibited by GPX or Sorafenib. The results show that GPX inhibits cell proliferation of Eca109 and KYSE150 at 5, 10, 15, 20 μM in a dose dependent manner Similar results are observed for SFB. It is demonstrated that GPX inhibits growth of human esophageal cancer cells in a dose dependent manner Example 6

Griffipavixanthone Induces Human Esophageal Cancer Cell Cycle Arrest 6.1 Materials RPMI1640 is purchased from Hyclone, fetal calf serum, penicillin and streptomycin are purchased from Invitrogen Corporation.

6.2 Methods

Eca109 and KYSE150 are cultured in RPMI1640 medium supplemented with 10% fetal calf serum, 100U/ml penicillin and 100 μg/ml streptomycin in a humidified atmosphere containing 5% $CO_2$ at 37° C. 0.25% trypsin is used for digestion and passage, cells under logarithmic growth phase are used in the experiment.

Eca109 and KYSE150 ($2 \times 10^5$ cells/well) are seeded to a 6-well place and treated with GPX or SFB (20 μM/well) for 48 hours. Cells are then harvested and fixed in 70% cold ethanol and stored 4° C. overnight. The cells are incubated with PI containing RNase A for 30 mins at 37° C., and are analyzed by flow cytometry (BD Biosciences Inc., Franklin Lakes, N.J., USA).

6.3 Results

Results are shown in FIG. 7A-D and FIG. 8A-D. GPX induces G2/M cell cycle arrest in Eca109 and KYSE150 at 5, 10, 15, 20 μM in a dose dependent manner; the results are in line with SFB. It is shown that GPX can induce G2/M arrest in a dose dependent manner to inhibit the growth of human esophageal cancer cells. Experimental data are expressed as mean±standard deviation, using SPSS18.0 statistical software for analysis, One-Way ANOVA for variance, comparison using Student t test, *P<0.05, P<0.01, *P<0.001 is considered as statistically significant difference.

Example 7

Griffipavixanthone Inhibit Lung Metastasis in Esophageal Cancer

7.1 Materials

RPMI1640 is purchased from Hyclone, fetal calf serum, penicillin and streptomycin are purchased from Invitrogen Corporation. Bouin's solution is purchased from Sigma.

7.2 Methods

Eca109 and KYSE150 are cultured in RPMI1640 medium supplemented with 10% fetal calf serum, 100U/ml penicillin and 100 μg/ml streptomycin in a humidified incubator containing 5% $CO_2$ at 37° C. 0.25% trypsin is used for digestion and passage; cells under logarithmic growth phase are used in the experiment.

KYSE150 cells ($1 \times 10^6$ cells/mouse) are intravenously injected into 6-week old male nude mice (Experimental Animal Center of the Chinese Academy of Science, Shanghai, China). The 6-week old male nude mice weight 20 g each. After injection of the cancer cells, the mice are divided into 3 groups randomly (n=8 in each group). DMSO, GPX (20 mg/kg) or 5-FU (20 mg/kg) are administered to the mice intraperitoneally every another day for 35 days. Body weight is measured every 2 days. 35 days later, lungs are removed and weighted. Using Bouin's solution, lungs are fixed, sliced and stained with HE to count number of lung nodules.

7.3 Results

Figure 9:
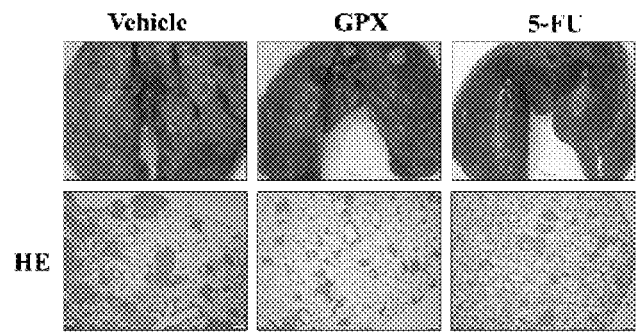
FIG. 9 are HE stainings of lung metastasis animal model having intravenous injection of 20 mg/kg Griffipavixanthone every another day for 35 days. Griffipavixanthone reduces lung nodules and area of pulmonary nodules in lung tissues.
Figure 10:
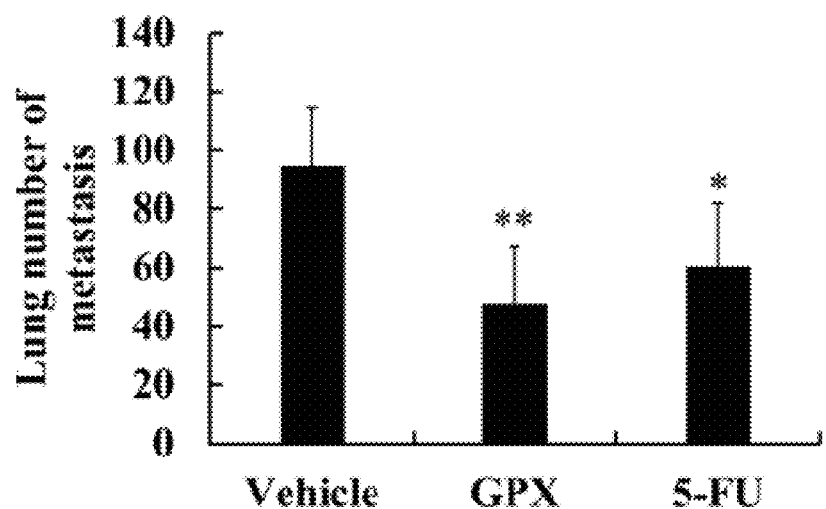
FIG. 10 is a bar chart showing statistical analysis of lung nodules of lung metastasis animal model having intravenous injection of 20 mg/kg Griffipavixanthone every another day for 35 days.
Figure 11:
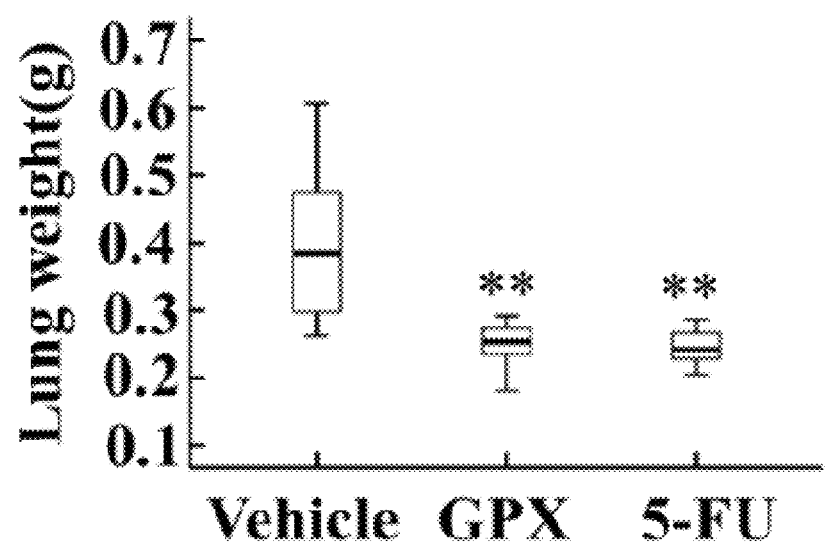
FIG. 11 is a chart showing weight of lung of lung metastasis animal model having intravenous injection of 20 mg/kg Griffipavixanthone every another day for 35 days.
Figure 12:
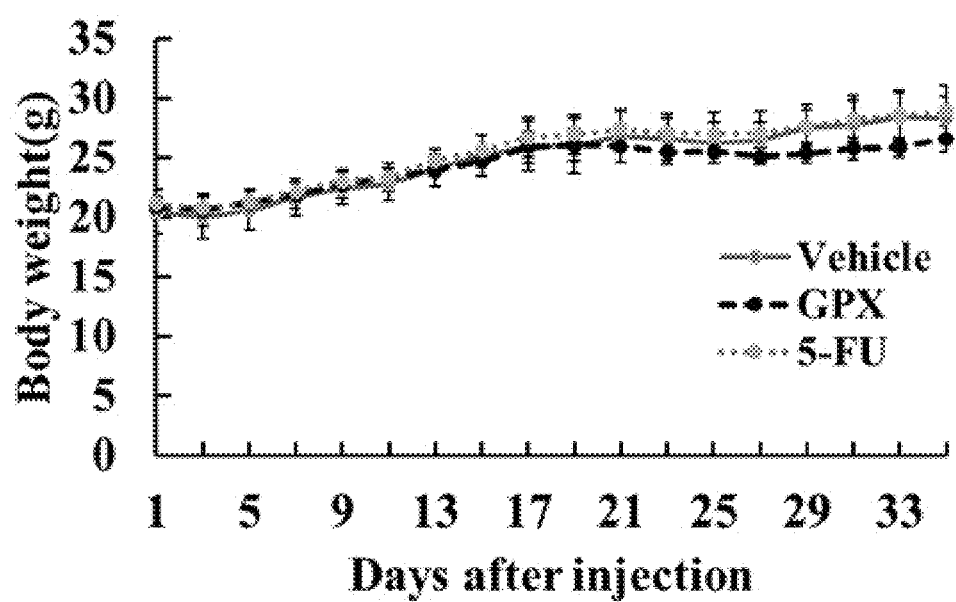
FIG. 12 shows mouse body weight having administered DMSO, GPX or 5-FU every another day for 35 days.

Results are shown in FIG. 9-11. 20 mg/kg GPX significantly inhibits lung metastasis of KYSE150; reduced number of lung tumor nodules, reduced lung weight and size of lung nodules are observed. FIG. 12 shows the body weight of mice. Larger metastatic foci are observed in the negative control group. On the other hand, metastatic foci are sparse and smaller in mice treated with GPX. It is shown that Griffipavixanthone inhibits esophageal cancer metastasis. Experimental data are expressed as mean±standard deviation, using SPSS18.0 statistical software for analysis, One-Way ANOVA for variance, comparison using Student t test, *P<0.05, P<0.01, *P<0.001 is considered as statistically significant difference.

Human equivalent dosage is translated from mouse dosage using the following equation:

$$HED (mg/kg) = \text{Animal dose (mg/kg) multiplied by} \frac{\text{Animal } Km}{\text{Human } Km}$$

(Reagan-Shaw et al. Dose translation from animal to human studies, The FASEB Journal, 22, 659-661 (2007). Disclosure thereof is incorporated herein by its entirety.) Human Km is 37; Mouse Km is 3. Therefore, based on the Example 7, the human equivalent dosage is 20 mg/kg×3/37=1.62 mg/kg.

As described above, although the invention is described herein with one or more embodiments, one of ordinary skill in the art will appreciate that the present invention can be modified without departing from the spirit and essence of the invention.

The invention claimed is:

1. A method of treating metastasis of esophageal cancer comprising administering a composition comprising a compound of Formula (I)

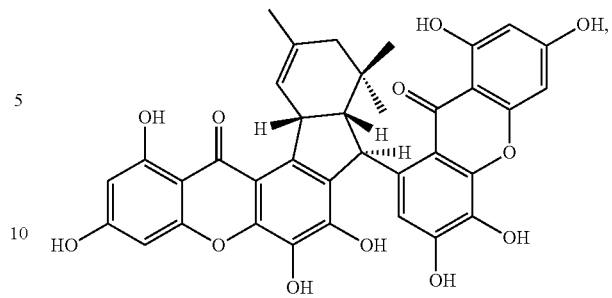

or a pharmaceutically acceptable salt, prodrug or hydrate thereof.

2. The method of claim 1, wherein the composition consists essentially of said compound of Formula (I), or said pharmaceutically acceptable salt, prodrug or hydrate thereof.

3. The method of claim 1, wherein said esophageal cancer is selected from human esophageal carcinoma cell Eca109 and human esophageal cancer cells KYSE150.

4. The method of claim 1, wherein said metastasis of esophageal cancer is lung metastasis.

5. The method of claim 1, wherein the composition comprises 1.62 mg of a compound of Formula (I), or a pharmaceutically acceptable salt, prodrug or hydrate thereof per kg of a subject in need thereof.

6. A method of treating esophageal cancer comprising administering a composition comprising a compound of Formula (I)

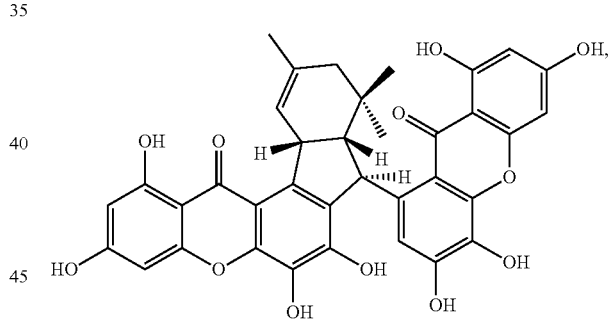

or a pharmaceutically acceptable salt, prodrug or hydrate thereof.

7. The method of claim 6, wherein the composition consists essentially of said compound of Formula (I), or said pharmaceutically acceptable salt, prodrug or hydrate thereof.

8. The method of claim 6, wherein said esophageal cancer is selected from human esophageal carcinoma cell Eca109 and human esophageal cancer cells KYSE150.

9. The method of claim 6, wherein the composition comprises 1.62 mg of a compound of Formula (I), or a pharmaceutically acceptable salt, prodrug or hydrate thereof per kg of a subject in need thereof.

* * * * *